United States Patent
Wilhelmsen et al.

(10) Patent No.: US 11,377,376 B2
(45) Date of Patent: Jul. 5, 2022

(54) PROCESS AND SYSTEM FOR MANAGING WATER IN A FOOD PREPARATION SINK

(71) Applicant: SMARTWASH SOLUTIONS LLC, Salinas, CA (US)

(72) Inventors: Eric Child Wilhelmsen, Milpitas, CA (US); Christopher Michael McGinnis, Seaside, CA (US); Danny Elmer Lindstrom, Salinas, CA (US); James M. Brennan, Pleasanton, CA (US)

(73) Assignee: SMARTWASH SOLUTIONS, LLC, Salinas, CA (US)

( * ) Notice: Subject to any disclaimer, the term of this patent is extended or adjusted under 35 U.S.C. 154(b) by 702 days.

(21) Appl. No.: 16/302,530

(22) PCT Filed: May 24, 2017

(86) PCT No.: PCT/US2017/034187
§ 371 (c)(1),
(2) Date: Nov. 16, 2018

(87) PCT Pub. No.: WO2017/205474
PCT Pub. Date: Nov. 30, 2017

(65) Prior Publication Data
US 2019/0177191 A1 Jun. 13, 2019

Related U.S. Application Data

(60) Provisional application No. 62/340,901, filed on May 24, 2016, provisional application No. 62/348,396, filed on Jun. 10, 2016.

(51) Int. Cl.
*C02F 1/50* (2006.01)
*A61L 2/28* (2006.01)
(Continued)

(52) U.S. Cl.
CPC .............. *C02F 1/505* (2013.01); *A47J 47/20* (2013.01); *A61L 2/16* (2013.01); *A61L 2/18* (2013.01);
(Continued)

(58) Field of Classification Search
CPC .... A47J 47/20; A61L 2/16; A61L 2/18; A61L 2/186; A61L 2/24; A61L 2/28;
(Continued)

(56) References Cited

U.S. PATENT DOCUMENTS 4,051,059 A  9/1977  Bowing et al.
4,248,827 A * 2/1981  Kitko .................. A61L 9/05
                                               4/227.1

(Continued)

OTHER PUBLICATIONS

International Search Report and Written Opinion for PCT/US2017/034187, dated Aug. 3, 2017.

*Primary Examiner* — Chester T Barry
(74) *Attorney, Agent, or Firm* — Patterson + Sheridan, LLP

(57) ABSTRACT

A method and system for managing water in a food preparation sink is provided. The system includes a sanitizer comprising a chemistry optimized for a food preparation sink water load, a delivery system configured to transport and deliver the sanitizer to the food preparation sink; and a verification element that is configured to be added to the water load in the food preparation sink and indicate when the water in the food preparation sink is not promoting growth or spread of bacteria.

19 Claims, 6 Drawing Sheets

(51) Int. Cl.
    *A61L 2/16*         (2006.01)
    *A61L 2/24*         (2006.01)
    *A47J 47/20*       (2019.01)
    *A61L 2/18*         (2006.01)
    *B08B 3/08*         (2006.01)
    *C02F 103/32*      (2006.01)

(52) U.S. Cl.
    CPC ................ *A61L 2/186* (2013.01); *A61L 2/24* (2013.01); *A61L 2/28* (2013.01); *B08B 3/08* (2013.01); *C02F 1/50* (2013.01); *A61L 2202/14* (2013.01); *C02F 2103/32* (2013.01); *C02F 2303/04* (2013.01)

(58) Field of Classification Search
    CPC ......... A61L 2202/14; B08B 3/08; C02F 1/50; C02F 1/505; C02F 2013/32; C02F 2303/04
    See application file for complete search history.

(56) References Cited

U.S. PATENT DOCUMENTS

| | | | |
|---|---|---|---|
| 9,052,303 | B2 | 6/2015 | Radmacher et al. |
| 2008/0035580 | A1* | 2/2008 | de Rijk .................. A01N 59/06 |
| | | | 210/748.11 |
| 2008/0242570 | A1 | 10/2008 | Carter et al. |
| 2012/0097256 | A1 | 4/2012 | Lopaciuk |
| 2012/0255623 | A1* | 10/2012 | Bell ........................ C02F 1/688 |
| | | | 137/268 |
| 2015/0197710 | A1 | 7/2015 | Garner et al. |
| 2015/0297770 | A1 | 10/2015 | Larson et al. |
| 2016/0095475 | A1 | 4/2016 | Brennan et al. |
| 2016/0205938 | A1* | 7/2016 | Jones ...................... C02F 1/688 |

\* cited by examiner

| Table 1 Buffer Adjuvant System for 12.5 gallon sink ||
|---|---|
| Ingredient | Amount (g) |
| Sodium phosphate monobasic | 14.97 |
| Propylene glycol | 2.37 |
| Lactic Acid | 2.63 |

FIG. 3

| Table 2 Formulation for 10 tablets of 26 mg each for verifying chlorine levels ||
|---|---|
| Ingredient | Amount (g) |
| Sodium thiosulfate | 0.037 g |
| Solublized starch | 0.25 g |
| Potassium iodide | 0.25 g |
| Mannitol | 2.00 g |
| Calcium stearate | 0.068 g |

FIG. 4

| Table 3: Liquid Adjuvant | |
|---|---|
| Ingredient | Amount (g) |
| Water | 25 |
| Sodium Phosphate Monobasic | 15 |
| Propylene Glycol | 2.4 |
| Lactic Acid | 8.8 |

FIG. 5

PROCESS AND SYSTEM FOR MANAGING WATER IN A FOOD PREPARATION SINK

CROSS-REFERENCE TO RELATED APPLICATIONS

This application is a national stage application under 35 U.S.C. 371 of International Application No. PCT/US2017/034187, filed May 24, 2017, which claims benefit of both U.S. Provisional Application No. 62/340,901, filed May 24, 2016 and U.S. Provisional Application No. 62/348,396, filed Jun. 10, 2016. The above applications are all incorporated by reference herein.

CLAIM OF PRIORITY

The present application claims benefit of U.S. Provisional Patent Application Ser. No. 62/340,901, filed May 24, 2016 and U.S. Provisional Patent Application Ser. No. 62/348,396, filed Jun. 10, 2016, assigned to the assignee hereof and hereby expressly incorporated by reference herein.

BACKGROUND

Field of the Disclosure

The subject matter disclosed herein generally relates to controlling and verifying control of cross contamination in a food preparation sink in a simple practical way.

Description of Related Art

Man has been washing dirt, grit and other foreign matter including bacteria from food for millennia. The human body can generally tolerate low levels of pathogens but it is unwise and inappropriate to allow them to grow or spread on food. Food is more pleasurable and potentially safer after washing. Increasingly, this washing has become a service that is purchased as part of buying a meal or other convenient forms of food. Such washing often occurs in a food preparation sink in the back of the store or restaurant. The water in this sink if improperly managed can be a food safety risk as it can promote pathogen growth and cross contamination.

Unfortunately, it is generally not practical to kill all pathogenic bacteria on fresh or raw food with a wash or rinse such as performed in a food preparation sink. This is particularly true for fresh produce. Treatments that can kill all the bacteria change the form of the product or reduce its quality. Using very hot water is an example of a treatment that could kill essentially all of the bacteria. Unfortunately, this would be a scalding hazard for the worker and would generally results in a markedly different product, something more akin to a cooked food. Very aggressive or long chemical treatments promote different changes such as chemically burning or wilting of food products before killing all of the bacteria on the food. Again this is particularly true of fresh produce. Thus one strives to find a balance between killing and controlling pathogens and maintaining the desirable attributes of a food. Obtaining the necessary control and management of the water to achieve this balance in food preparation sinks remains challenging.

Accordingly there is a desire to provide a method and/or system for controlling and verifying control of cross contamination in a food preparation sink.

BRIEF SUMMARY

According to an embodiment, a system for managing water in a food preparation sink is provided. The system includes a sanitizer including a chemistry optimized for a food preparation sink water load, a delivery system configured to transport and deliver the sanitizer to the food preparation sink, and a verification element that is configured to be added to the water load in the food preparation sink and indicate that the water in the food preparation sink is not promoting growth or spread of bacteria.

In addition to one or more of the features described above, or as an alternative, further embodiments may include wherein the delivery system includes a premeasured amount of sanitizer in at least one from a group consisting of a bag, pouch, tablet, and ampoule.

In addition to one or more of the features described above, or as an alternative, further embodiments may include wherein the sanitizer includes chlorine, wherein a pH of the water is between 4 and 6 with a free chlorine concentration of at least 2 ppm in the presence of an adjuvant.

In addition to one or more of the features described above, or as an alternative, further embodiments may include an adjuvant, wherein the adjuvant is a diol or polyol and is configured to reduce outgassing potential with a buffer system to stabilize the pH between 4 and 6, and is configured to slow the reaction with organics and enhance lethality.

In addition to one or more of the features described above, or as an alternative, further embodiments may include wherein the sanitizer includes at least one of hydrogen peroxide and peroxyacids, wherein equilibrium between the hydrogen peroxide and the peroxyacids is provided when organic acids are mixed with hydrogen peroxide.

In addition to one or more of the features described above, or as an alternative, further embodiments may include wherein the organic acids are less than 1% of the sanitizer and water mix.

In addition to one or more of the features described above, or as an alternative, further embodiments may include wherein the hydrogen peroxide level does not exceed 100 ppm in the sanitizer and water mix.

In addition to one or more of the features described above, or as an alternative, further embodiments may include wherein a minimum level for microbial control is equal to or greater than 25 ppm in the sanitizer and water mix.

In addition to one or more of the features described above, or as an alternative, further embodiments may include wherein the sanitizer includes silver 10 ns.

In addition to one or more of the features described above, or as an alternative, further embodiments may include wherein the silver ions are stabilized in either citric or lactic acid at levels around 5%.

In addition to one or more of the features described above, or as an alternative, further embodiments may include wherein stability in the preparation sink is enhanced by either additional citric and lactic acid, wherein 2 ppm is a minimum lower level.

In addition to one or more of the features described above, or as an alternative, further embodiments may include wherein the verification element can provide a visual indicator of a critical parameter and a critical value that can be assessed with a simple pass no pass test.

In addition to one or more of the features described above, or as an alternative, further embodiments may include wherein the simple pass no pass test for chlorine can confirm that the chlorine in a food preparation sink remains above 2 ppm.

In addition to one or more of the features described above, or as an alternative, further embodiments may include wherein the verification element is provided as a tablet, wherein the tablet is added to a portion of water and the tablet will turn blue when sufficient chlorine remains.

In addition to one or more of the features described above, or as an alternative, further embodiments may include wherein the sanitizer includes a premeasured dose of lactic acid and hydrogen peroxide, wherein the peroxide level is limited to a maximum of 80 ppm, and wherein the lactic acid is limited by the tolerance of the product to be treated, wherein the tolerance is less than 1%.

In addition to one or more of the features described above, or as an alternative, further embodiments may include wherein silver ion are included in 5% citric acid to make the water in the food preparation sink 10 ppm silver.

In addition to one or more of the features described above, or as an alternative, further embodiments may include wherein the delivery system is a two packet delivery system, and wherein the verification element is provided as a tablet based verification tool.

In addition to one or more of the features described above, or as an alternative, further embodiments may include wherein a first packet of the two packet delivery system contain a buffer system and chemistry optimization system which includes monobasic and dibasic sodium monophosphate and either propylene glycol or glycerin.

In addition to one or more of the features described above, or as an alternative, further embodiments may include wherein a second packet of the two packet delivery system includes a second component 1s the sanitizer component, wherein the second component is calcium hypochlorite.

In addition to one or more of the features described above, or as an alternative, further embodiments may include wherein the tablet is based on a pass no pass test, and wherein three adaptable variables are tested, wherein the three adaptable variables include the amount of sodium thiosulfate or other suitable reducing agent, the volume of water to react, and the critical failure where the color change is desired.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

FIG. 3 is an example of a buffer adjuvant system, in accordance with certain aspects of the present disclosure.

FIG. 4 is an example of a formulation for ten tablets for verifying chlorine levels, in accordance with aspects of the present disclosure.

FIG. 5 is an example of a liquid adjuvant, in accordance with aspects of the present disclosure.

To facilitate understanding, identical reference numerals have been used, where possible, to designate identical elements that are common to the figures. It is contemplated that elements disclosed in one aspect may be beneficially utilized on other aspects without specific recitation.

DETAILED DESCRIPTION

Figure 1:
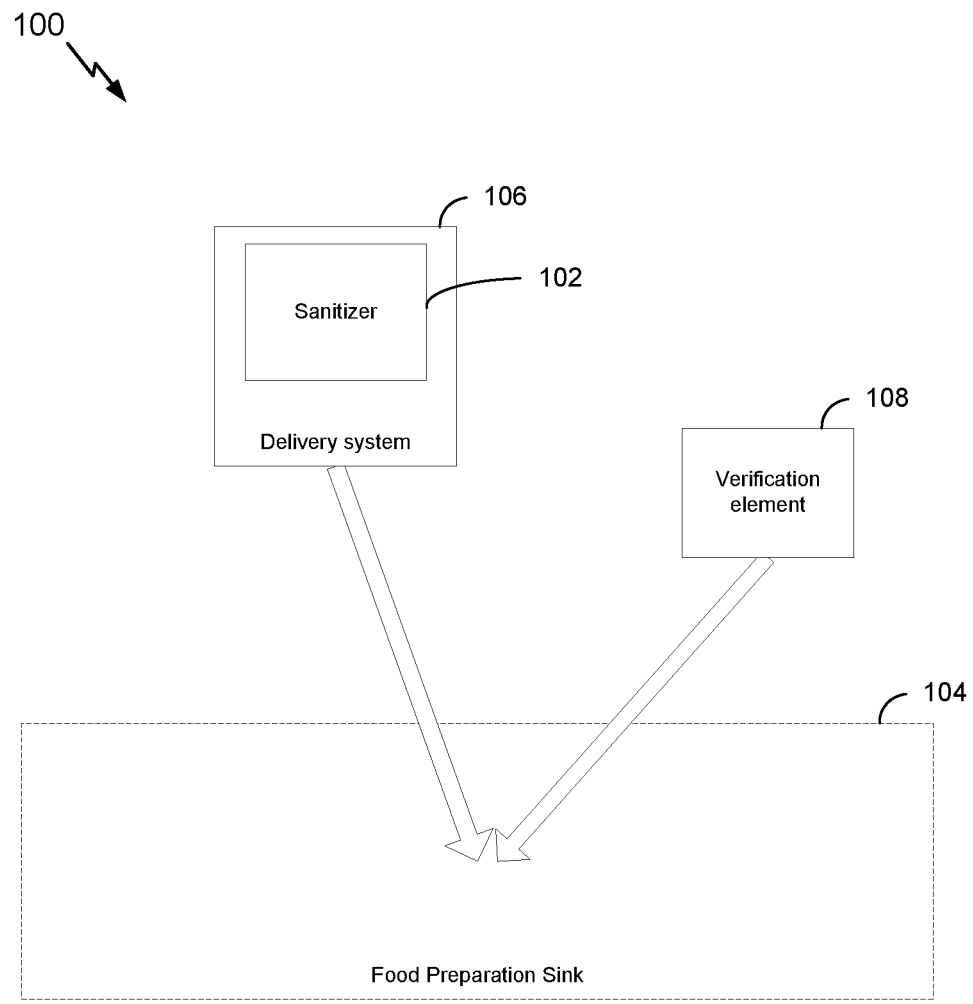
FIG. 1 is a block diagram illustrating an example system for managing water in a food preparation sink, in accordance with certain aspects of the present disclosure.

In one embodiment, an approach and system for optimizing sanitizer use in a food preparation sinks based on premeasured doses of stabilization components and sanitizer is presented. This system also provides verification that the sanitizer exceeds the minimum safe threshold and therefore controls cross-contamination and bacterial growth.

There is a short list of chemical treatments that can provide moderate lethality and can control the growth and spread of pathogens in food preparation sinks. Given that the water in the food preparation sink is in intimate contact with the food product, only materials approved for direct food contact can be considered such as chlorine, chlorine dioxide, ozone, hydrogen peroxide, a peroxyacid, and silver ions. Under some conditions rinsing is required. Each of these materials has regulatory and intrinsic restrictions on its use. Each of these materials are managed to obtain optimal performance. All of these materials are depleted during use and can therefore cease to mitigate pathogen growth and spreading when depleted.

Various vendors have and do offer systems to deliver one or more of these sanitizers to the sink by diluting a concentrate. Systems range from simply measuring a specified amount of a solution into a sink to automated dosing systems. Other systems use an onsite generation system to produce a sanitizer and deliver it to the sink. None of these approaches seem to have reached the optimum for simplicity and reliability. Adding a piece of equipment that needs to be maintained and often requires a consumable is not a good fit in this food preparation area. The lack of affirmative information that the solution in the sink is ready or still ready for use presents an opportunity for problems.

An added complication is the impact of the treated food item on the water and the sanitizer chemistry. Extractables from the food react with the sanitizer. Reacted sanitizers are no longer available for preventing growth and cross contamination in the food preparation sink. These reactions determine at least in part, how often the water in the food preparation sink needs to be replaced and recharged with chemicals. This consumption and need for recharging requires management. A better approach to managing the water in a food preparation sink is needed.

The concept of simplifying the management of the water in a food preparation sink and thereby make it easy for a food preparation worker to execute and verify their efforts will improve the food safety of the restaurant. To realize the concept and effectively manage the wash process in a food preparation sink, several elements are brought together including a simple easy delivery system, optimization of the water and sanitizer chemistry, and a verification that water in the preparation sink is not promoting to growth or spreading bacteria Each of these areas is complex with numerous options so each area will be discussed separately.

Automated dosing and generation systems are less desirable as too complex for this operating environment. The capital cost of such systems is difficult to justify in this low technology work area. Instead, premeasured amounts yield the most reliable and convenient delivery system. Such deliver can take many forms including premeasured amounts in bags or pouches, tablets, or ampoules which are particularly useful for liquid formulations. Although users can be asked to measure out an amount as with a measuring cup or spoon, this procedure reduces the reliability of the process and increases the challenge of verification. It is important that the proper amounts of the water management materials are used. Over and under dosing are both undesirable. Specific examples are provided below.

The preference for premeasured delivery promotes the use of chlorine, hydrogen peroxide, peroxyacids and silver ion as the sanitizers of choice. These can be delivered in stable packaged forms. Other allowed sanitizers such as ozone are not stable enough to be delivered in premeasured form and may instead be generated on site. Chlorine dioxide is also unstable and may instead be generated on site. One can consider exotic forms of the other listed materials such as electrolyzed water, a form of chlorine but these differences impact mostly the way the sanitizer was generated and can be considered as included in these few families. For these listed materials, we can consider how to optimize the chemistry for use in a food preparation sink.

According to one or more cases, as shown in FIG. 1, a system 100 for managing water in a food preparation sink includes a sanitizer 102 that includes a chemistry optimized for a food preparation sink water load. A delivery system 106 can be configured to transport and deliver the sanitizer 102 to a food preparation sink 104. The system may further include a verification element 108 that is configured to be added to the water load in the food preparation sink 104 and indicate that the water in the food preparation sink 104 is not promoting growth or spread of bacteria.

Considering first the chemical requirements for optimizing chlorine use, there are several parameters to consider. The most important is the chlorine concentration. This concentration is set high enough to control cross contamination and prevent growth of pathogens in the water. The chemical form and therefore the effectiveness of chlorine is controlled by the pH of the water. And finally, there are adjuvants that can enhance the lethality of the chlorine and retard other less desirable reactions. In simplest terms, a pH of between about 4 and 6 with a free chlorine concentration of at least about 2 ppm in the presence of the right adjuvants provides a good start for providing an optimized chlorine wash. Washes can be further optimized for treating different items. For example, adding an adjuvant system including a diol or polyol to reduce outgassing potential with a buffer system to stabilize the pH as desired between about 4 and 6 will slow the reaction with organics and enhance lethality. For quality reasons, one does not generally want to exceed 50 ppm free chlorine in a wash sink.

Figure 2:
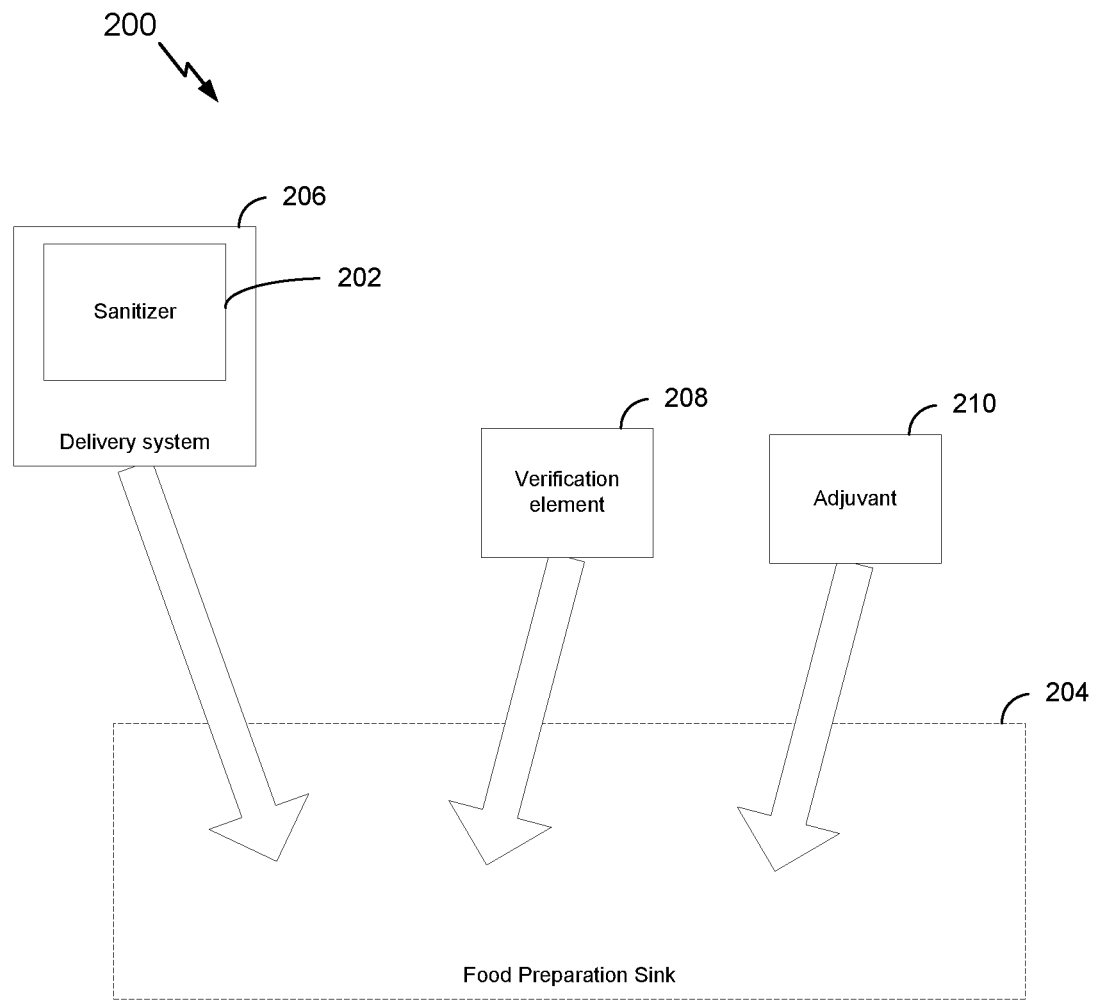
FIG. 2 is a block diagram illustrating another example system for managing water in a food preparation sink that includes an adjuvant, in accordance with certain aspects of the present disclosure.

Thus, according to another example, as shown in FIG. 2, a system 200 for managing water in a food preparation sink includes a sanitizer 202 that includes a chemistry optimized for a food preparation sink water load. A delivery system 206 can be configured to transport and deliver the sanitizer 202 to a food preparation sink 204. The system may further include a verification element 208 that is configured to be added to the water load in the food preparation sink 204 and indicate that the water in the food preparation sink 204 is not promoting growth or spread of bacteria. This system 200 may also include an adjuvant 210 as shown and discussed herein. Other arrangements of the system may also be provided as discussed in embodiments herein. For example, the delivery system may be a two part system and may be provided in multiple different forms such as, but not limited to, pouches and/or tablets. Similarly, the verification element and the adjuvant may be provided in one or more forms. Further, according to one or more embodiments, the sanitizer, verification element, and adjuvant may be provided together, individually, or any sub combination thereof.

To optimize the use of hydrogen peroxide and peroxyacids, there is an intersection. Both systems become largely the same as there is equilibrium between the hydrogen peroxide and the peroxyacids when organic acids are mixed with hydrogen peroxide. Acetic acid is the most common but similar chemistry can be obtained with other organic acids. Usually simpler acids are preferred. The amount of acid is limited by the potential to damage the product chemically, usually less than 1% but there is a time dependence on tolerated doses. High concentrations will chemically burn the product. The peroxide level should not generally exceed 100 ppm. Some products and systems will require chelators to reduce the disproportionation of the peroxide to maintain lethality. The minimum level for the desired microbial control is system dependent but generally about 25 ppm.

And finally we can consider the case where silver ions are used. These could be generated on site but it is more practical to stabilize the ions in either citric or lactic acid at levels around 5%. The ions should to be protected from light during storage as the ion will abstract and electron for almost any material. Silver is a very potent oxidant. Silver ion is only effective in solution so chloride, bromide, sulfide and phosphate ions are controlled to prevent precipitation. This constraint may limit the utility of silver ion in food preparation sinks. Stability in the preparation sink is enhanced by either additional citric and lactic acid. Currently regulatory requirements mandate a removal step for use as a sanitizer. For the desired microbial control, 2 ppm is reasonable critical lower level.

And lastly, we turn to verification as the last element. All verification is predicated on a previously completed validation. This is done by knowing the boundary conditions that satisfy the process requirements and then verifying that an appropriate process was executed. In the current food processing sink system described herein, there is the implicit assumption made that a set of optimized chemistries has been shown to prevent microbial growth and cross contamination have been identified. We will return to how to generate validation data after discussing verification the last element of this system.

A verification process provides the means to assure that the various control parameters that define the validated conditions have been met. The verification process can also provide reasonable assurance that they were met at the time of the process. There is a temptation to invoke a full laboratory and instrumentation for this verification. However this level of analytical support is more complicated than required for a well-designed food preparation sink management system. Generally, there is a critical parameter and a critical value that can be assessed with a simple pass no pass test. This does not imply that more complicated quantitative tests cannot be used just that they are not required for the verification process.

An example will illustrate this concept. As described below, a simple pass no pass test for chlorine can confirm that the chlorine in a food preparation sink remains above 2 ppm In this test, a tablet is added to a portion of water and it will turn blue when sufficient chlorine remains. This test can be done by almost any worker and yields a simple to interpret result. Alternatively, one could use one of the various titrations or colorimetric methods to quantitate the level of chlorine present. For the titrations, a burette or an alternative fluid measuring device, a standardized reagent that may lack stability, appropriate lab ware, and an operator trained to perform and interpret the test are provided. For a colorimetric procedure, a color comparator of some type is included. Spectrophotometers are a common choice but color wheels and color charts are still in use.

To enable one or more embodiments disclosed herein, a short discussion of the validation process is warranted. As discussed previously, one works to prevent bacterial growth and cross-contamination in the food preparation sink. There are not standardized methods for either of these indices of success. However, there are concepts that have been used to develop one or more embodiments disclosed herein that warrant mention. These are research approaches that are not appropriate for use in a food preparation area.

For the growth of bacteria, one can use an approach like the AOAC sanitizer test as a model. If a particular chemistry provides lethality in this test, it will not promote growth. The basis for this test is simple. A high level inoculum is added to the solution to be tested. After a specific time interval, the solution is quenched and the survivors are enumerated. Any significant lethality is this test indicates that growth is not supported. Obviously other approaches can be taken but the short time frame of use for a sink of water justifies this simple direct approach.

For assaying cross contamination, an alternative direct approach is useful in order to look at the ability of the chemistry to prevent migration. In a suitable test system, one allows inoculated product the opportunity to infect other product and measures the resulting infection level. There are several parameters to control to have a useful metric and basis for comparison including inoculation level, ratio of inoculated product to uninoculated product, and the time of exposure. An inoculation level of about 104 organisms per gram has been useful. A one to on ratio of inoculated product to uninoculated is a good place to work experimentally. The time of exposure should be consistent with the planned treatment times, usually from 1-5 minutes. Comparing the transfer rates for chlorine free water as a negative reference and for 15 ppm chlorine with proper pH control as a bench mark for control has proven useful.

Turning to more specific embodiments of the water management system, it is worth pointing out two failed approaches for using a single package delivery system. A mixture of sodium phosphates, propylene glycol and calcium hypochlorite was blending when it burst into flame releasing chlorine gas. This paste definitely lacked stability and is definitely unsuitable for this use. A liquid product replacing the calcium hypochlorite with a solution of sodium hypochlorite did not flame but did react exothermically and also releases chlorine gas. Given these results other approaches are needed.

Figure 6:
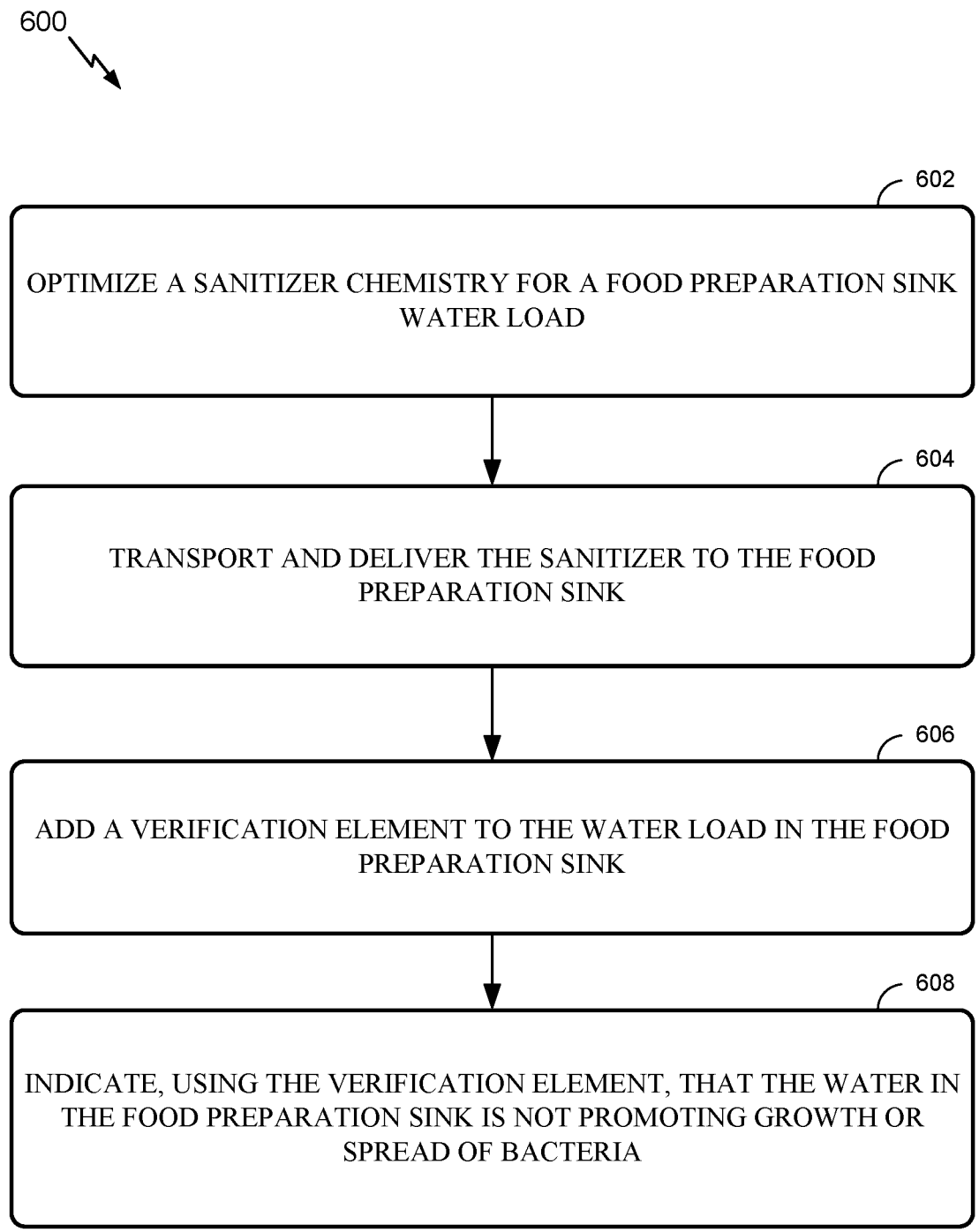
FIG. 6 illustrates example operations for managing water in a food preparation sink, in accordance with aspects of the present disclosure.

For example, according to one or more embodiments, operations 600 may be provided for managing water in a good preparation sink as shown in FIG. 6. The operations 600 may include, at block 602, optimizing a sanitizer's chemistry for a food preparation sink water load. Further, operations 600 may include, at block 603, transporting and delivering the sanitizer to the food preparation sink using a delivery system. Operations 600, at block 606, further include adding a verification element to the water load in the food preparation sink. Finally, operation 600 may include, at block 608, indicating, using the verification element, that the water in the food preparation sink is not promoting growth or spread of bacteria.

Another embodiment is based on a premeasured dose of lactic acid and hydrogen peroxide. For quality reasons, the peroxide level is limited to a maximum of 80 ppm if it is to be used without a potable water rinse. The lactic acid is limited by the tolerance of the product to be treated, generally less than 1%. These doses can be packages variously to provide a premeasured dose based on the volume to be treated, generally around 12 gallons. Such calculations based on weight or volume and concentration are generally known and need no elaboration. Bottles are more expensive than pouches or other flexible packaging. For this embodiment, the components can be delivered to the user separately or together. The acid can be altered to another organic acid. Acetic acid would be a common choice. However, most any food grade acid would increase the lethality of the peroxide and will also improve cross contamination control in the food preparation sink.

Another embodiment based using silver includes enough silver ion in 5% citric acid to make the sink 10 ppm silver. A commercial product is available with 2400 ppm silver that works well. This is again a concentration volume calculation that includes a specific volume in the sink. A second package contains lactic acid and glycerin sufficient to make the water in the sink about 1% lactic acid and about 0.5% glycerin. Given that both of these components are liquids, the packaging is water tight. Pouches, ampoules and bottles can all work. These will be quite small given that the food preparation sinks are generally between 10 and 15 gallons. It is provided that it is easy to completely remove the material from whatever package is selected.

A more preferred embodiment of a sink management system build around chlorine includes a two packet delivery system and a tablet based verification tool. The first packet contain a buffer system and chemistry optimization system which includes monobasic and dibasic sodium monophosphate and either propylene glycol or glycerin. This mixture is pasty but can be handled with appropriate filling equipment to deliver a 5 mm buffer at pH 6.2. This material can be packaged in a small polyethylene pouch. Flat lay tubing or preformed bags work well. Other choices come into play with automated filling.

According to one or more examples, a buffer adjuvant system for a 12.5 gallon sink may be provided. Specifically, as shown in FIG. 3, the buffer adjuvant system for a gallon sink may include sodium phosphate monobasic, propylene glycol, and lactic acid in the amounts as set out in Table 1 shown in FIG. 3.

Although the formulation presented here seems to have general applicability, it is easy to foresee conditions where the optimal mixture will be changed. For products releasing higher levels of organics, it may be desirable to increase the concentration of the adjuvant mix. For some applications, a different source of geminal hydroxyl groups will be desired including glycerin and various food grade polyols. Clearly, other buffers can be used including potassium phosphate salts. The acid can be changed as well. Ultimately, it is important to remember that the goal is facilitate the simple management of the wash water.

The second component is the sanitizer component in this case calcium hypochlorite. For the same sink, 6.3 gram calcium hypochlorite can be included. However, we have found that this material degrades over time and loses potency. It is recommended that the chlorine content be assayed and the weight adjusted to deliver the desired level of chlorine. This assay can be done by titration against standardized thiosulfate. The degradation of this component will limit the shelf life to between 6 months and 1 year. It should not be packaged in a metalized foil to attempt to extend its shelf life. The foil will blacken and corrode. Instead a sandwiched barrier package is preferred. However, this packaging is mostly to reduce the slight chlorine smell associated with the material when it is stored in a hermetic container. Barrier packaging is readily available from film converters and will not be elaborated here.

In some cases, the use of sodium hypochlorite as a source of chlorine can be seen as desirable but shipping liquids is more restrictive than dry powders. Sodium hypochlorite is commercially available in 4 to 10% chlorine solutions. It can also be assayed by titration with standardized sodium thiosulfate. The delivered solutions should not be too concentrated as these are a hazard for the user. As a practical suggestion, the delivered solution should be less than 10,000 ppm.

Verification that the desired process has been performed is a critical element. For the peroxide and chlorine based, a preferred embodiment is the tablet based pass no pass assay described above. An assay of this type has three adaptable variables including the amount of sodium thiosulfate or other suitable reducing agent, the volume of water to react, and the critical failure where the color change is desired. The tablet includes mostly mannitol to speed dissolution but most any highly soluble not reactive carbohydrate could be used. A tablet press is used for manufacturing these tablets. Tablets are used because the reagent amount is too small to be weighed in this working environment. Sugar alcohols are especially good prompting the selection of mannitol. A small amount of calcium stearate is added as a binding agent to allow the tablet to better withstand mechanical action. As shown in FIG. 4, a specific blend for 10 tablets to assert that chlorine is over 4 ppm is shown in Table 2.

To adjust these tablets for other levels of chlorine or for peroxide, the level of thiosulfate is adjusted up or down. This can be handled by titrating a known level of the desired oxidant with thiosulfate and determining how much thiosulfate to include for the amount of oxidant in the selected volume of water. In this specific case, 100 ml of the water to be tested is mixed with a single tablet and shaken to dissolve the table. If the solution turns blue, there is still sufficient chlorine. The water in a sink should be replaced before the reaction mixture stops turning blue.

Clearly, one could make use of the chemistry optimization taught here and use other verification methods but these add to the complexity of the management process. However, it is important to note that these more complex methods will yield quantitative results that are useful for developing standard practices. Standard practices would include having an estimate as to how much product can be washed in a sink of treated water before it should be replaced. Determining that a process has failed after product has been treated, it not a desirable outcome. Nevertheless, knowing allows remedial action to be taken.

According to one or more embodiments, an adjuvant system can include all the substances, which includes at least sodium phosphate monobasic, propylene glycol, and lactic acid, dissolved in water. This delivery method provides a user with a liquid that includes the other substances already dissolved thereby eliminating the steps of adding water to the dry adjuvant and dissolving it in the water prior to use. Specifically, as shown in FIG. 5, an embodiment of the adjuvant system that affords greater ease of use and easier manufacture is listed in Table 3.

This mixture forms a slightly syrupy solution that is easy to fill into pouches or bottles which eases packaging. According to one or more embodiments, when manufacturing the adjuvant adding the water to the mixing device first is provided because the dry ingredients tend to case harden and can disrupt mixing. This modification increases the weight of the adjuvant mixture which can add shipping costs. According to one or more embodiments, this adjuvant can be used with either a calcium hypochlorite powder or with a liquid sodium hypochlorite solution.

Another embodiment can be made where all of the wash components are placed in a single package. This increases the volume and mass of the treatment product but does yield a single component system. The water in the above formulation needs to be increased to about 300 grams. The chlorine concentration in this single component system should not exceed 10,000 ppm. The limits are not sharp as greater shelf life is achieved as the concentration is reduced therefore other embodiments with reduced concentrations can be provided. There are situation where this single component system that includes all wash components will be preferred such as location that prioritize ease of use and do not mind the additional weight and size of the single component system. In other embodiments, for general use the more concentrated solution with a separate sanitizer component is selected when the additional step of combining the components is possible thereby avoiding the additional weight and size of the single component system.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions, combinations, sub-combinations, or equivalent arrangements not heretofore described, but which are commensurate with the scope of the present disclosure. Additionally, while various embodiments of the present disclosure have been described, it is to be understood that aspects of the present disclosure may include only some of the described embodiments.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Accordingly, the present disclosure is not to be seen as limited by the foregoing description, but is only limited by the scope of the appended claims.

What is claimed is:

1. A system for managing water in a food preparation sink, the system comprising:
   a sanitizer configured to come into contact with a food product and to prevent microbial growth for a water load in the food preparation sink, wherein the sanitizer comprises chlorine;
   a delivery system configured to transport and deliver the sanitizer to the food preparation sink;
   an adjuvant configured to enhance a lethality of the sanitizer; and
   a verification tablet that is configured to be added to the water load in the food preparation sink and indicate that the water load in the food preparation sink is not promoting the microbial growth.

2. A system for managing water in a food preparation sink, the system comprising:
   a sanitizer configured to come into contact with a food product and to prevent microbial growth for a water load in the food preparation sink, wherein the sanitizer comprises chlorine;
   a delivery system configured to transport and deliver the sanitizer to the food preparation sink, wherein the delivery system includes a premeasured amount of the sanitizer in at least one from a group consisting of a bag, a pouch, and an ampoule; and
   a verification tablet that is configured to be added to the water load in the food preparation sink and indicate that the water load in the food preparation sink is not promoting the microbial growth.

3. The system of claim 1, wherein a pH of the water load is between 4 and 6 with a free chlorine concentration of at least 2 ppm in the presence of the adjuvant.

4. The system of claim 1, wherein the adjuvant is a diol or polyol, is configured to reduce outgassing potential with a buffer system to stabilize a pH of the water load between 4 and 6, and is configured to slow a reaction of the sanitizer with organics.

5. The system of claim 1, wherein the verification tablet provides a visual indicator of a critical parameter and a critical value that can be assessed with a pass/no pass test.

6. The system of claim 5, wherein the pass/no pass test is for chlorine and is configured to confirm that the chlorine in the food preparation sink remains above 2 ppm.

7. The system of claim 5, wherein the verification tablet is configured to turn blue when sufficient chlorine remains in the water load.

8. The system of claim 1, wherein the delivery system is a two-packet delivery system.

9. The system of claim 8, wherein a first packet of the two-packet delivery system contains a buffer system and a chemistry system which includes monobasic and dibasic sodium monophosphate and either propylene glycol or glycerin.

10. The system of claim 8, wherein a second packet of the two-packet delivery system includes the sanitizer, wherein the sanitizer is calcium hypochlorite.

11. The system of claim 1, wherein the adjuvant comprises sodium phosphate monobasic, propylene glycol, lactic acid, and water.

12. The system of claim 11, wherein the adjuvant comprises:
    15 grams of sodium phosphate monobasic;
    2.4 grams of propylene glycol;
    8.8 grams of lactic acid; and
    25 grams of water.

13. The system of claim 1, wherein the sanitizer is provided as a liquid in a water solution.

14. The system of claim 1, wherein the adjuvant comprises lactic acid and glycerin.

15. A method for managing water in a food preparation sink, comprising:
    delivering, with a delivery system, a sanitizer to a water load in the food preparation sink, wherein the sanitizer comprises chlorine and is configured to control microbial growth in the water load and to come into contact with a food product;
    adding a verification tablet to the water load;
    delivering, to the water load, an adjuvant configured to enhance a lethality of the sanitizer; and
    determining, using the verification tablet, whether the water load in the food preparation sink is promoting microbial growth.

16. The method of claim 15, wherein the adjuvant comprises lactic acid and glycerin.

17. The method of claim 15, wherein a pH of the water load is between 4 and 6 with a free chlorine concentration of at least 2 ppm in the presence of the adjuvant.

18. The system of claim 1, wherein the verification tablet comprises mannitol.

19. The system of claim 18, wherein the verification tablet further comprises calcium stearate.

* * * * *